United States Patent [19]

Nishimura

[11] Patent Number: 4,958,307
[45] Date of Patent: Sep. 18, 1990

[54] ROLL MARK INSPECTION APPARATUS

[75] Inventor: Seikichi Nishimura, Kawasaki, Japan

[73] Assignee: Kabushiki Kaisha Toshiba, Kawasaki, Japan

[21] Appl. No.: 273,029

[22] Filed: Nov. 18, 1988

[30] Foreign Application Priority Data

Nov. 20, 1987 [JP] Japan .................. 62-293466
Nov. 20, 1987 [JP] Japan .................. 62-293467

[51] Int. Cl.$^5$ .................. G06F 15/20; G01N 33/24
[52] U.S. Cl. .................. 364/551.01; 364/469;
364/507; 364/552; 250/562; 356/237; 340/675
[58] Field of Search .......... 364/469, 506, 507, 551.01,
364/552; 356/237; 340/673, 675, 676; 250/559, 562, 563

[56] References Cited

U.S. PATENT DOCUMENTS

| | | | |
|---|---|---|---|
| 4,292,672 | 9/1981 | Southgate | 364/507 |
| 4,334,282 | 6/1982 | Whitehouse | 364/507 |
| 4,495,587 | 1/1985 | Plante et al. | 364/507 |
| 4,519,041 | 5/1985 | Fant et al. | 364/552 |
| 4,578,770 | 3/1986 | Mitani | 364/551.01 |
| 4,587,617 | 5/1986 | Barker et al. | 364/507 |
| 4,677,578 | 6/1987 | Wright et al. | 364/552 |
| 4,719,583 | 1/1988 | Takafuji et al. | 364/551.01 |

FOREIGN PATENT DOCUMENTS

52-13952  4/1977  Japan .
57-59353  4/1982  Japan .
58-156842  9/1983  Japan .

Primary Examiner—Gary Chin
Assistant Examiner—Brian M. Mattson
Attorney, Agent, or Firm—Oblon, Spivak, McClelland, Maier & Neustadt

[57] ABSTRACT

A roll mark inspection apparatus for a system for rolling and moving a strip uses reduction rolls. An image sensor scans widthwise the strip which is rolled and moved by the reduction rolls and outputs an image signal representing a surface state of the strip per unit width. A clock generator generates a clock signal synchronized with the running of the strip moved by the reduction rolls. An autocorrelation calculator sequentially receives the image signal in synchronism with the clock signal, and performs a predetermined autocorrelation calculation processing on the contents of the received signal and outputs an autocorrelation value. A comparator compares a predetermined comparison value for discriminating information corresponding to a roll mark on the surface of the strip with the autocorrelation value, and outputs a roll mark signal discriminated from the autocorrelation value by the predetermined comparison value. A CRT display device updates and displays image information corresponding to the roll mark signal each time the strip runs by a predetermined distance corresponding to a circumferential length of the reduction rolls.

22 Claims, 9 Drawing Sheets

ROLL MARK INSPECTION APPARATUS

BACKGROUND OF THE INVENTION

1. Field of the Invention

The present invention relates to a roll mark inspection apparatus for inspecting periodic roll marks (periodic defects) formed on a belt-like running material, such as a steel strip, an aluminum strip, or a copper strip, due to a roll surface speck existing on a reduction roll in rolling lines.

2. Description of the Related Art

In rolling lines, periodic roll marks are sometimes formed by a specked roll on a belt-like running material or a material to be rolled. In a press line using a plurality of rolls having different diameters, roll marks having different periods are formed on a material to be rolled.

Figure 4A:
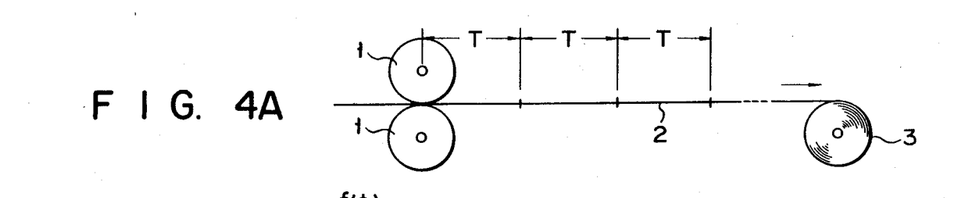
FIG. 4A is a schematic view for explaining how strip 2 rolled by rolls 1 is wound onto coil 3.

A technique for inspecting each periodic roll mark is disclosed in Japanese Pat. Disclosure (Kokai) No. 58-156842. In this technique, an autocorrelation function of roll mark data is calculated to inspect each periodic roll mark. A principle of the technique will be described below. As shown in FIG. 4A, belt-like running material (to be referred to as a strip hereinafter) 2 to be rolled by roll 1 runs in an arrow direction and is wound at its terminal end to become coil 3.

Figure 4B:
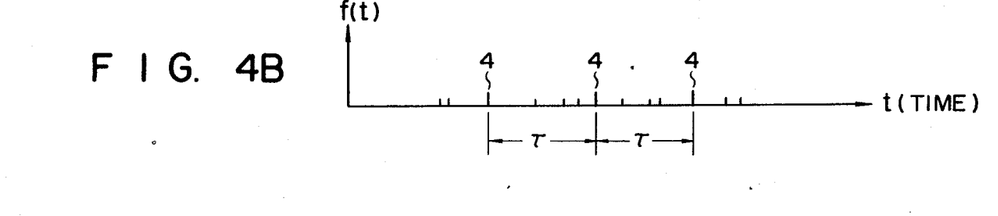
FIG. 4B is a graph showing roll mark signals 4 before effecting autocorrelation calculation, which includes roll marks formed at period τ corresponding to circumferential length T of rolls 1.
Figure 5A:
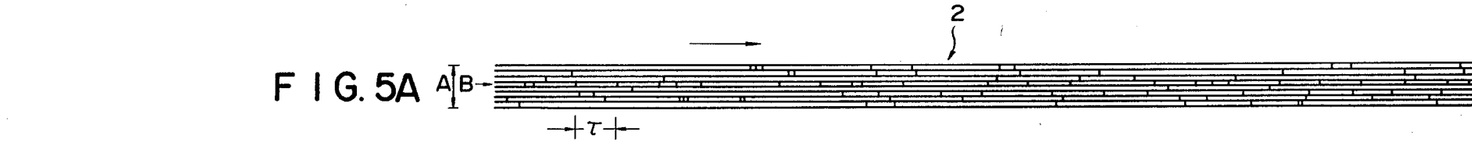
FIG. 5A is a schematic view showing the surface of strip 2 including a roll mark.
Figures 5B, 5C:
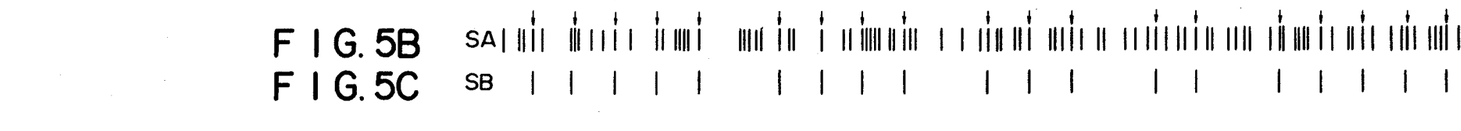
FIG. 5B is a schematic view showing signal SA corresponding to roll marks formed across the entire width A of strip 2.
FIG. 5C is a schematic view showing signal SB corresponding to roll marks formed across ⅛ of width B of strip 2.

In this process, if specks exist on the surface of roll 1, roll marks are formed on the surface of strip 2, and signals 4 (FIG. 4B), representing the roll marks, have a periodicity. FIG. 5A shows how the roll mark is produced. In FIG. 5B, reference symbol SA represents roll mark signals formed across an entire width of strip 2. In FIG. 5C, reference symbol SB represents roll mark signals formed on ⅛ of the entire width. Arrows "↓" represent roll mark signals to be inspected which apparently have periodicity. Other lines represent signals of random marks. Interval $\tau$ between arrows "↓" is equal to the circumferential length of roll 1.

Figure 6:
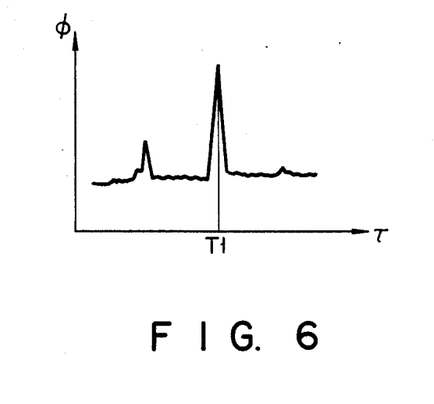
FIG. 6 is a graph showing a relationship between autocorrelation function $\phi$ and period τ of signal SA in FIG. 5B or signal SB in FIG. 5C.

Autocorrelation function $\phi$ of the roll mark signal (SA or SB) has a high peak at period $\tau$ (timing T1 in FIG. 6) corresponding to the circumferential length of roll 1. Therefore, the periodicity of roll marks to be inspected can be accurately detected by examining this peak.

Figure 7:
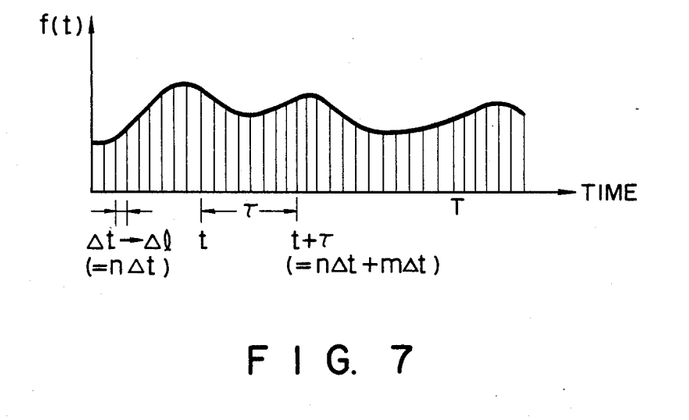
FIG. 7 is a histogram in which signal SA in FIG. 5B or signal SB in FIG. 5C is obtained for each time interval $\Delta t$.

FIG. 7 is a histogram showing the roll mark signals (SA or SB) obtained at each time interval $\Delta t$. Assuming that the envelope of the histogram is function f(t) of time t, then autocorrelation function $\phi(\tau)$ is given by either of the following equations:

$$\phi(\tau) = \lim_{T \to \infty} (1/2T) \int_{-t}^{+t} f(t) \cdot f(t + \tau) \cdot dt \quad (1)$$

$$\phi(\tau) = \lim_{T \to \infty} (1/T) \int_{0}^{t} f(t) \cdot f(t + \tau) \cdot dt \quad (2)$$

where T is an interval for obtaining the autocorrelation function.

More specifically, the autocorrelation function is calculated as follows:

$$\phi(m\Delta t) = (1/T) \sum_{n=0}^{N} f(n \cdot \Delta t) \cdot f(n \cdot \Delta t + m \cdot \Delta t) \cdot \Delta t \quad (3)$$

$$= (1/N) \sum_{n=0}^{N} f(n \cdot \Delta t) \cdot f(n \cdot \Delta t + m \cdot \Delta t)$$

On the basis of the above equation (3), calculations are repeatedly performed for each instantaneous time interval $\Delta t$ while variables m and n are changed from 1 to M and from 0 to N, respectively, as follows:

$$\phi(\Delta t) = (1/N) \sum_{n=0}^{N} f(n \cdot \Delta t) \cdot f(\overline{n + 1} \cdot \Delta t)$$

$$\phi(2\Delta t) = (1/N) \sum_{n=0}^{N} f(n \cdot \Delta t) \cdot f(\overline{n + 2} \cdot \Delta t)$$

$$\phi(3\Delta t) = (1/N) \sum_{n=0}^{N} f(n \cdot \Delta t) \cdot f(\overline{n + 3} \cdot \Delta t)$$

$$\phi(M\Delta t) = (1/N) \sum_{n=0}^{N} f(n \cdot \Delta t) \cdot f(\overline{n + M} \cdot \Delta t) \quad (4)$$

$$= (1/N) \{f(0) \cdot f(0 + M \cdot \Delta t) + \quad (4\text{-}0)$$
$$f(\Delta t) \cdot f(\Delta t + M \cdot \Delta t) + \quad (4\text{-}1)$$
$$f(2 \cdot \Delta t) \cdot f(2 \cdot \Delta t + M \cdot \Delta t) + \quad (4\text{-}2)$$
$$f(3 \cdot \Delta t) \cdot f(3 \cdot \Delta t + M \cdot \Delta t) + \quad (4\text{-}3)$$

$$f(N \cdot \Delta t) \cdot f(N \cdot \Delta + M \cdot \Delta t)\} \quad (4\text{-}N)$$

In the above equations, the autocorrelation can be obtained by calculating a product of a roll mark signal preceded by circumferential length $M \cdot \Delta t$ of roll 1 each time strip 2 advances by $\Delta t$, and by adding this product to a preceding calculated value, as represented by the equations (4-0) to (4-N) Then, the obtained autocorrelation is compared with a predetermined set value (roll mark detection level L) to inspect each periodic roll mark.

As a result, all the periodic roll marks formed by various rolls having roll specks can be simultaneously inspected, while an S/N ratio of the roll mark signal can be largely increased.

In rolling lines, the production rate is very high, e.g. 30 tons/min. For this reason, if roll marks are formed on the surface of a strip and inspection of the roll mark is delayed even slightly, a large amount of defective products (strip) are manufactured. Therefore, a demand has arisen for an apparatus capable of rapidly inspecting the roll mark.

In order to inspect the roll mark by the above technique, however, considerably long inspection length T of, at least 1,000 m, is required. In some cases, several thousands meters are required.

Further, since considerably long inspection length T is required to inspect the roll mark, a time for inspecting the roll mark is prolonged.

Figure 8A:
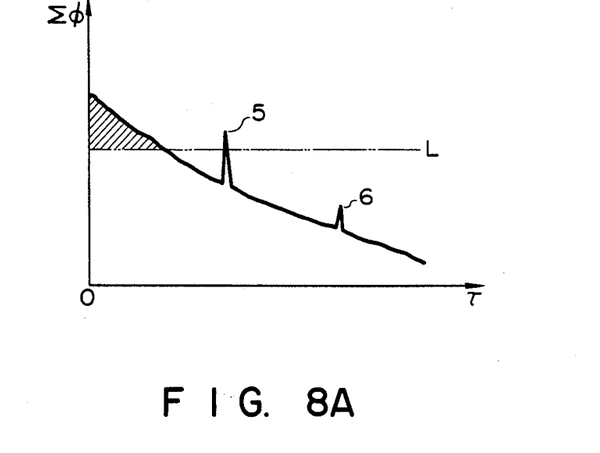
FIG. 8A is a graph showing a relationship between period τ and autocorrelation function $\Sigma\phi$ including a background power level other than signals 5 and 6 representing roll marks.

In addition, as shown in FIG. 8A, a background power level of the autocorrelation function ($\Sigma\phi$) calculated from roll mark signal data is increased as interval $\tau$ for calculating the autocorrelation function is reduced, and the background power level is reduced as interval $\tau$ is increased. Accordingly, values of peaks 5 and 6, each representing the roll mark, are reduced as interval $\tau$ is increased (FIG. 8A shows that the height of peak 6 at long interval τ is lower than that of peak 5 at short interval τ).

Figure 8B:
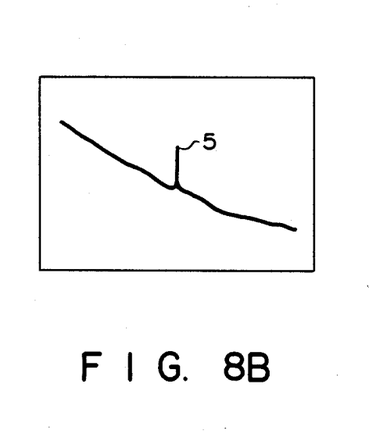
FIG. 8B is a graph in which roll mark signal 6 is missed and only roll mark signal 5 is displayed when the presence/absence of roll marks is detected at level L in FIG. 8A.

Therefore, when the autocorrelation value of each of roll mark peaks 5 and 6 is compared with roll mark detection level L, if this level L is fixed as shown in FIG. 8A, roll mark 6 obtained at long interval τ cannot be inspected although roll mark 5 can be inspected as shown in FIG. 8B. In addition, in this case, background noises in the region of short interval τ (hatched area in FIG. 8A) are erroneously detected as if roll marks are involved therein.

As described above, the conventional technique is adversely affected by the background power level (noise) and cannot therefore always inspect all roll marks having different periods.

SUMMARY OF THE INVENTION

It is, therefore, a first object of the present invention to provide a roll mark inspection apparatus capable of rapidly inspecting a periodic roll mark and displaying the roll mark at a circumferential length pitch of a reduction roll.

It is a second object of the present invention to provide a roll mark inspection apparatus capable of inspecting all periodically formed roll marks without being adversely affected by a background power level.

The roll mark inspection apparatus of the present invention has a means for storing roll mark data in an image memory having a memory area corresponding to the circumferential length of the roll, the roll mark data being output from an inspection head for scanning in a width direction a belt-like running material which runs while it is urged against a roll, sequentially reading out the roll mark data stored in the image memory in synchronism with a running rate of the belt-like running material to calculate an autocorrelation value, and comparing the autocorrelation value with a predetermined set value, thereby inspecting a periodic roll mark formed on the belt-like running material. In order to achieve the above first object of the present invention, this apparatus comprises: a sync signal generating means for generating a sync signal synchronized with the running rate of the belt-like running material; a latch means for receiving the sync signal from the sync signal generating means to detect that the belt-like running material runs by the maximum roll circumferential length ($\pi$ Dmax) to be measured, and latching an output representing comparison between the autocorrelation value and the set value; and a display means for displaying the comparison result output latched by the latch means.

With the above arrangement, a roll mark data autocorrelation function depending on a running time difference of the belt-like running material corresponding to the roll circumferential length is calculated, and then calculated autocorrelation values are sequentially compared with the set value to obtain a maximum value of the calculated autocorrelation values. Then, the latch means detects, by means of the sync signal from the sync signal generating means, that the belt-like running material runs by the roll circumferential length and latches the comparison result output. The latched comparison result output is displayed on the display means, e.g. displayed as one raster on a CRT display device.

In addition, the roll mark inspection apparatus of the present invention has a means for storing roll mark data in an image memory, the roll mark data being inspected by an inspection head for scanning widthwise a belt-like running material which runs while it is urged against a roll, calculating an autocorrelation value of the roll mark data obtained in a predetermined inspection length (e.g. 1000 m) for automatic roll mark judgment along a running direction of the belt-like running material, and converting the autocorrelation value into, e.g. a binary value in accordance with a roll mark detection level by a comparator, thereby inspecting a periodic roll mark formed on the belt-like running material by specks existing on the roll. In order to achieve the above second object of the present invention, this apparatus comprises: a smoother for smoothing the autocorrelation value obtained in the predetermined inspection length; and a roll mark detection level generator for supplying an output obtained by multiplying a smoothed output from the smoother a predetermined number of times as a roll mark detection level corresponding to a background power level to the comparator.

With the above arrangement, the autocorrelation value obtained in the predetermined inspection length of the belt-like running material is smoothed by the smoother, and a smoothed output is multiplied with a predetermined number by the roll mark detection level generator to obtain a roll mark detection level which increases/decreases in accordance with the magnitude of the background power level.

DETAILED DESCRIPTION OF THE PREFERRED EMBODIMENTS

An embodiment of the present invention will be described in detail below with reference to the accompanying drawings. In these drawings, the same reference numerals denote the parts having the same functions and a detailed description of the parts already described will be omitted or simplified.

Figure 1:
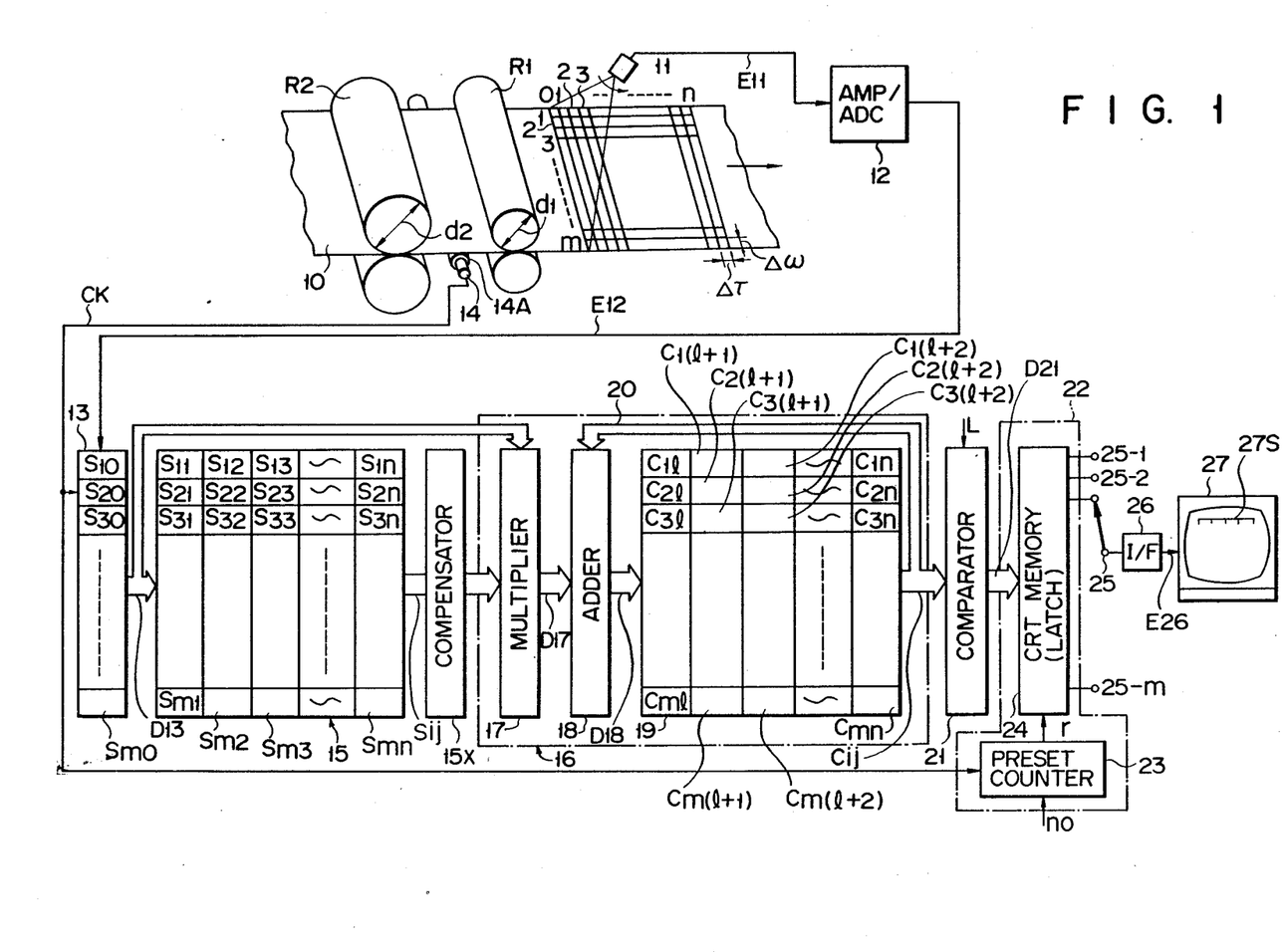
FIG. 1 is a block diagram showing an arrangement of a roll mark inspection apparatus according to a first embodiment of the present invention.

FIG. 1 is a block diagram showing a roll mark inspection apparatus corresponding to the first object of the present invention. In FIG. 1, strip 10 moves at a constant rate in a direction indicated by the arrow while it is urged against rolls R1 and R2 having different diameters d1 and d2, respectively (the number of rolls may be arbitrarily selected).

Optical inspection head 11 (e.g., line scanning type linear array CCD camera) is arranged above strip 10. Strip 10 is illuminated by a high-pressure mercury lamp or the like. Head 11 scans strip 10 in a direction perpendicular to the running direction, i.e., the width and outputs signal E11 representing roll marks within a predetermined unit length range.

The unit length range is determined by unit length $\Delta\tau$ in the running direction of strip 10 and width ($\Delta\omega \times$ m) thereof. Reference symbol $\Delta\omega$ represents a unit length widthwise of strip 10. In this case, $\Delta\tau \times \Delta\omega$ forms one pixel Sij.

Roll mark signal E11 is amplified by amplifier 12, A/D-converted to be binary signal E12, and then supplied to storage register (serial/parallel converter) 13.

Sync signal generator 14 is arranged below strip 10 and outputs sync signal CK synchronized with the moving rate of strip 10. Generator 14 may comprise a pulse generator or rotary encoder which rotates coaxially with rubber roller 14A in contact with strip 10 and generates N pulses per revolution.

Register 13 stores binary roll mark signal E12 sequentially in units of pixels ($\Delta\tau \times \Delta\omega$) in synchronism with signal CK from generator 14. Roll mark data stored in register 13 is data (S10 to Sm0, i.e., data of $\Delta\omega \times$ m pixels) of one column scanned in the width direction of strip 10. Data D13 of one scanned column is parallel output to image memory 15.

Each time strip 10 advances by one unit length $\Delta\tau$, memory 15 stores parallel input data D13 and outputs the stored one scanned column data sequentially from the oldest one. Memory 15 must have a memory capacity of m $\times$ n pixels where:

$$m \geq \text{width of strip } 10 / \Delta\omega \qquad \ldots (5)$$

n=circumferential length $\pi d2/\Delta\tau$ of a roll having the largest diameter Dmax (since d2>d1 in FIG. 1, d2=Dmax is used to determine n). A storage state of one column data is represented by rewriting jth column data Sij with (j−1)th column data Si(j−1), i.e., by the following relation:

$$Sij \leftarrow Si(j-1) \qquad \ldots (6)$$

(where i=1 to m and j=1 to n)

In the above relation, Sij represents each pixel. In the roll mark data, the running direction of strip 10, i.e., S11, S12, S13, ..., S1n corresponds to a row direction and the width direction thereof, i.e., S11, S21, S31, ..., Sm1 corresponds to a column direction.

Therefore, memory 15 sequentially stores data D13 corresponding to each unit length $\Delta\tau$ of strip 10 in an amount corresponding to a circumferential length of roll R2.

Data D13 output from register 13 is supplied to autocorrelation calculator 16. Calculator 16 can execute autocorrelation function calculation represented by equation (4) and comprises multiplier 17, adder 18, and calculated value register 19. Multiplier 17 and adder 18 execute calculations of the following relation (7):

$$Cij \leftarrow SiO \times Sij + Cij \qquad \ldots (7)$$

(i=1 to m, j=1 to n)

Calculation result Cij is stored in register 19. As a result, register 19 stores a calculated value of the right-hand side of equation (4):

$$(1/N) \sum_{n=0}^{N} f(n \cdot \Delta t) \cdot \overline{f(n + M) \cdot \Delta t)} \qquad (8)$$

By executing such calculations, an S/N ratio of a signal component of periodic roll marks is increased in proportion to $\sqrt{N}$ (an integrating effect) For this reasons, even a small roll mark can be inspected from noise components.

Data bus 20 performs feedback to add Cij at the right-hand side of equation (7). Obtained autocorrelation value data (Cij) is supplied to comparator 21.

Comparator 21 sequentially compares data Cij of one row, e.g., C1, C1 (e+1), ..., C1n with preset value L having a predetermined threshold value, and outputs maximum value D21 of the autocorrelation calculated value data (C1 to C1n) of one row. This comparison is executed for each autocorrelation value data of one row.

In an actual rolling line, since a period varies due to sliding between the rolls and strip 10 or the like, compensator 15X is provided to compensate for this variation. Compensator 15X executes the next compensation calculation on the basis of periodic variation $\pm \gamma$ [mm] which is experimentally obtained beforehand:

$$Sij = \text{maximum of } (Si(j-p), Si(j-p+1), \ldots, Sij, Si(j+1), \ldots, Si+p) \ldots \qquad (9)$$

where $p = \gamma/\Delta\tau$. Equation (9) adopts the maximum value of variation $Si(j \pm p)$ corresponding to $\pm \gamma/\tau (= \pm p)$ of output data Sij from register 13.

Latch circuit 22 receives signal CK supplied from generator 14 and representing that strip 10 advances by circumferential length $\pi d2$ of roll R2, and latches comparison result output D21 from comparator 21. Circuit 22 comprises preset counter 23 and CRT memory 24. Preset count n0, representing the number of signals CK generated while strip 10 advances by length $\pi d2$, is preset in counter 23. When the count of signals CK reaches value n0, counter 23 sends latch signal r to memory 24. When memory 24 receives signal r, memory 24 latches and stores comparison result D21 from comparator 21.

Channel selector 25 having contacts 25-1, 25-2 to 25-m for the respective rows is connected to memory 24. CRT display device 27 is connected to selector 25 through CRT interface 26.

An operation of the apparatus having the above arrangement will be described below. When strip 10 runs in the arrow direction, head 11 optically scans strip 10 in the width direction and outputs roll mark signal E11. Signal E11 is amplified by amplifier 12 and binarized to become binary signal E12, and signal E12 is supplied to and stored in register 13.

Sync signal generator 14 outputs sync signal CK synchronized with the running rate of strip 10. Thus, signal E12 is stored as roll mark data of S10 to Sm0 of one column widthwise of strip 10, i.e., of pixels $\Delta\omega \times m$ in synchronism with signal CK in register 13. Each time strip 10 runs by unit length $\Delta\tau$, roll mark data D13 of the next column widthwise of strip 10 is stored in register 13 by signal CK.

In this manner, each time data D13 of one column widthwise of strip 10 is supplied to register 13, preceding data D13 stored in register 13 is parallel output to image memory 15.

Each time memory 15 receives data D13 of one column, memory 15 parallel shifts the stored data of one preceding column.

The storage capacity of memory 15 in a row (lengthwise) direction corresponds to roll circumferential length $\pi d2$. When strip 10 runs by length $\pi d2$, i.e., shifts by an amount corresponding to maximum roll circumferential length $\pi d2/\Delta\tau$, data D13 of one column is output to autocorrelation calculator 16 through compensator 15X.

Multiplier 17 in calculator 16 multiplies roll mark data Sij of one column (e.g., S1n, S2n, ..., Smn) output from memory 15 by data D13 of one column (e.g., S10, S20, ..., Sm0) from register 13 in units of pixels and supplies multiplication result D17 to adder 18. Adder 18 adds calculation result Cij (e.g., C1n, C2n, ..., Cmn) from register 19 to result D17 from multiplier 17 in units of pixels and supplies addition result D18 to calculated value register 19. In this manner, register 19 stores the calculated values of the right-hand side of equation (4).

Figure 2:
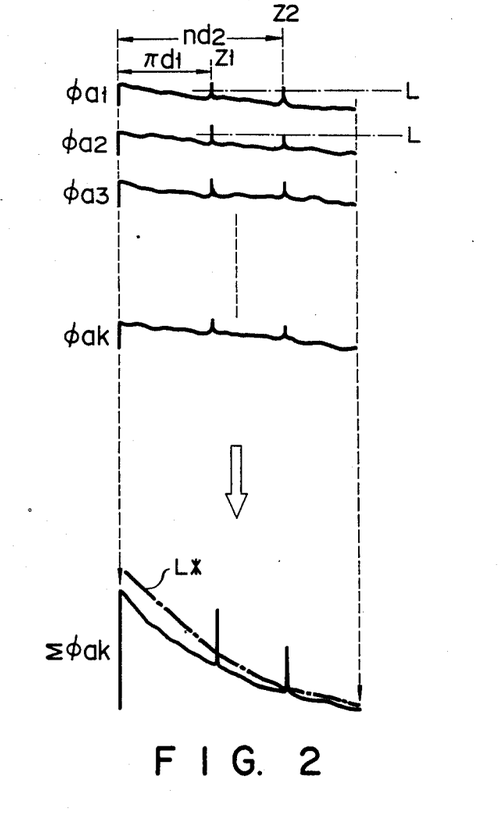
FIG. 2 is a graph showing a calculation result of an autocorrelation function $\phi_{ak}$ calculated in the apparatus of FIG. 1.

In this case, the calculated values are those as shown in FIG. 2. For example, an autocorrelation value in the running direction of strip 10 becomes $\phi a1$ by values C1e, C1(e+1), C1(e+2), ..., C1n, and becomes $\phi b1$ (not shown) by values C2e, C2(e+1), C2(e+2), ..., C2n. In FIG. 2, reference symbol Z1 denotes a roll mark formed by roll R1 having roll diameter d1; Z2, a roll mark formed by roll R2 having roll diameter d2.

Values $\phi a1$, $\phi b1$, ... are simultaneously supplied to comparator 21 and compared with preset value L.

Signal CK output from generator 14 is supplied to preset counter 23, and counter 23 count signals CK. When strip 10 runs by circumferential length $\pi d2$ of roll R2, the count of counter 23 reaches preset count value n0, and counter 23 supplies latch signal r to CRT memory 24.

Figure 3:
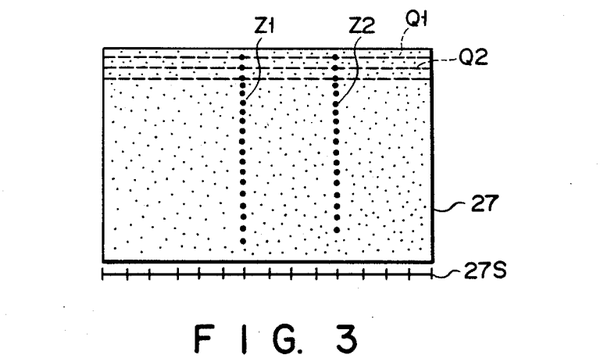
FIG. 3 is a schematic view showing a roll mark displayed on a CRT as a result of an autocorrelation calculation.

Memory 24 which receives signal r latches and stores the comparison result from comparator 21. Therefore, memory 24 stores the comparison result of value $\phi a1$ with value L, the comparison result of value $\phi b1$ with value L, ..., for each row of data D18 in register 19. If selector 25 is connected to 25-1, the comparison result of value $\phi a1$ with value L is supplied from memory 24 to CRT interface 26. Interface 26 converts the comparison result of value $\phi a1$ with value L into image signal E26 and supplies signal E26 to CRT display device 27 to be displayed thereon as shown in FIG. 3. When the next latch signal r is supplied to memory 24, the comparison result of value $\phi a2$ with value L at this time is supplied to interface 26. The comparison result is converted into image signal E26 of one raster Q2 and displayed on device 27 as shown in FIG. 3. As a result, the inspection area corresponding to roll circumferential length $\pi d2$, i.e., autocorrelation values $\phi a1$, $\phi a2$, ... of roll mark data of one row consisting of pixels S11 to S1n, is displayed as rasters Q1, Q2, ... each time strip 10 runs by length $\pi d2$.

As described above, in the above embodiment, sync signal CK from sync signal generator 14 is received to ensure that strip 10 runs by roll circumferential length $\pi d2$, and then a comparison result output from comparator 21 is latched and displayed as one raster on CRT display device 27. Therefore, each time strip 10 runs by the roll circumferential length, a calculation result of an autocorrelation function is displayed so that the state of roll marks formed on strip 10 can be monitored. As a result, a periodic roll mark can be immediately inspected by monitoring the display screen of device 27 because roll marks, e.g., Z1 and Z2 continuously appear as shown in FIG. 3.

In addition, if device 27 includes scale 27S corresponding to the roll circumferential length on its display screen, the period of the roll marks can be visually detected to easily check which of rolls R1 and R2—having different diameters—has the roll mark. In addition, since roll marks continuously and repeatedly appear on the CRT display screen, even a small roll mark can be easily detected. Therefore, since the presence of roll marks on the roll can be immediately detected, this ensures that a large amount of defective products is not manufactured, thereby improving productivity.

As has been described above in detail, according to the embodiment of the present invention, periodic roll marks can be immediately inspected by observing patterns displayed on a CRT on which the pitch of generation of the roll mark can also be displayed.

The present invention is not limited to the above embodiment but can be modified without departing from the scope of the present invention. For example, in the above embodiment, data binarized by set value L in comparator 21 is used for display. However, data D21 may be converted into a multilevel value by setting a plurality of levels of value L, thereby displaying a roll mark with two or more gradation levels.

Figure 11A:
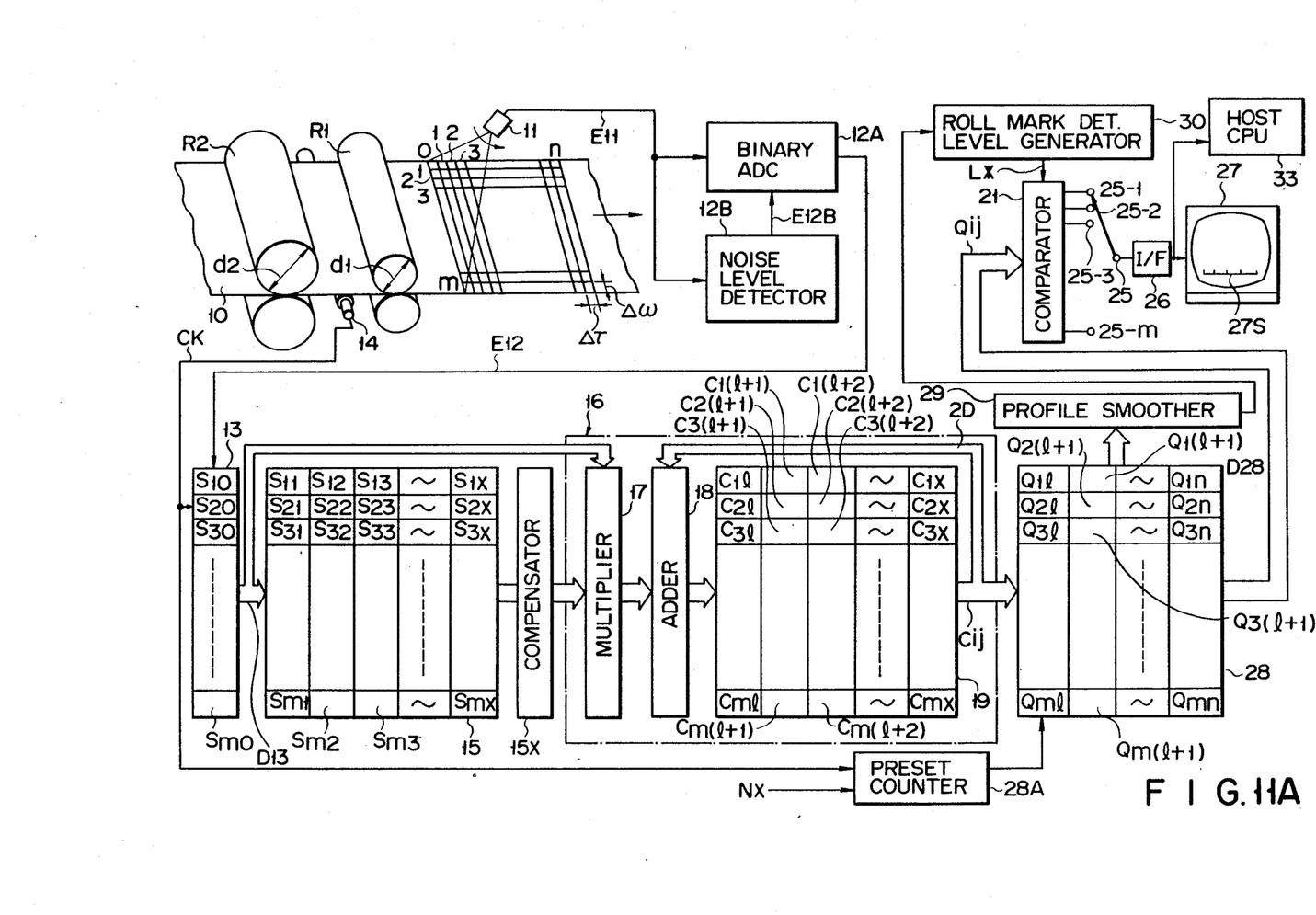
FIG. 11A is a block diagram showing an arrangement of a roll mark inspection apparatus according to a second embodiment of the present invention.

FIG. 11A is a block diagram showing an arrangement of a roll mark inspection apparatus according to the second object of the present invention. In FIG. 11A, strip 10 moves at a constant rate in a direction indicated by an arrow while it is urged by rolls R1 and R2 having different diameters d1 and d2. Optical inspection head 11 is arranged above strip 10. Head 11 optically scans strip 10 widthwise and outputs roll mark signal E11 for predetermined unit length area ($\Delta\omega \times m$). Signal E11 is supplied to binary circuit 12A and then stored in register (serial/parallel converter) 13 as roll mark data E12.

Binary set level (threshold level) E12B of circuit 12A can be changed in accordance with a noise level detected by noise level detector 12B. That is, level E12B is automatically changed in accordance with noise levels corresponding to different surface roughness values of roll R1 and R2.

Detector 12B detects an average level of noise components in a predetermined area (scanning range of head 11) of strip 10 each time strip 10 runs by unit length $\Delta\tau$. Detector 12B prepares level 12B corresponding to the detected average noise level, and supplies it to circuit 12A.

More specifically, detector 12B comprises an amplifier for amplifying signal E11, a rectifier for rectifying the amplified signal, a filter for removing a ripple component from the rectified signal, and a circuit for adjusting a DC level of the signal output from the filter and outputting the adjusted DC level as binary set level E12B. Circuit 12A may comprise a comparator using level E12B as a comparison reference level. In order to eliminate an influence on signal E12 due to noise of a low-frequency component, circuit 12A may include a two-dimensional high-pass filter.

Similar to the embodiment shown in FIG. 1, output E12 from circuit 12A is supplied to register 13, memory 15, compensator 15X, and autocorrelation calculator 16. Autocorrelation value data Cij calculated by calculator 16 is supplied to autocorrelation profile memory 28 of the next stage.

Memory 28 has a memory area identical to that of calculated value register 19 so that calculation results C1e to Cmn of register 19 are supplied to and stored in Q1e to Qmn, respectively. The timing of supplying results C1e to Cmn to memory 28 is determined when strip 10 runs by, e.g., 1,000 m. The timing can be determined by detecting the count "0" of down counter 28A which is preset by predetermined number Nx and down-counts the pulse of signal CK. In this case, preset number Nx is selected to correspond to, for example, 1,000 m.

Profile smoother 29 can smooth the autocorrelation values of each row stored in memory 28, e.g., values Q1e, Q1(e+1) to Q1n, and Q2e, Q2(e+1) to Q2n, respectively.

Figure 9:
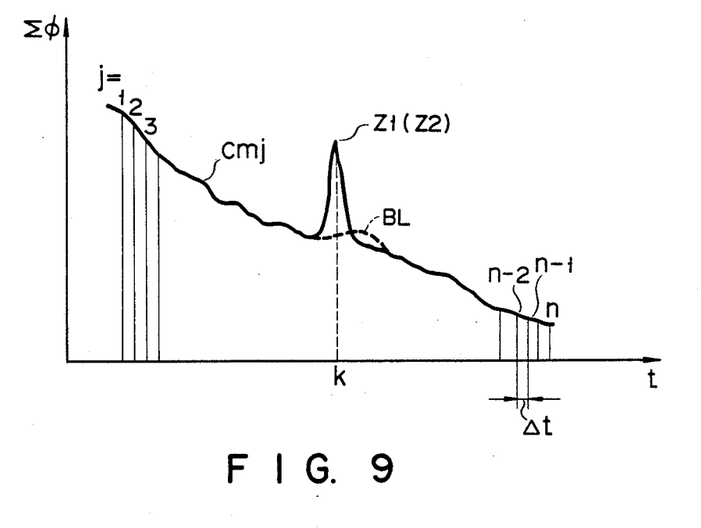
FIG. 9 is a histogram showing an accumulation result of autocorrelation value $C_{mj}$ on an mth column in a width direction of strip 10.

Smoother 29 performs smoothing processing as follows. Assume that input data to smoother 29 is autocorrelation data Cmj having a peak at point Cmk (j=k) as shown in FIG. 9. In this case, smoothing processing value $\overline{Cmk}$ at point Cmk is represented by the following equation:

$$\overline{Cmk} = [Cm(k - l) + Cm(k - l + 1) + \ldots + Cm(k - l + 0) + Cm(k + l) + \ldots + Cm(k + l)]/(2l - 1) \quad (10)$$

$\overline{Cmk}$ in equation (10) is an average value of length $2e\cdot\Delta\tau$ (moving distance of strip 10) to be autocorrelated and provides a histogram with no peak as indicated by broken line BL in FIG. 9.

In FIG. 9, symbol $\Sigma\phi$ exemplifies an accumulation result of autocorrelation value Cmj of an mth column in the width direction of strip 10. (Peak Z1 or Z2 of Cmj represents a roll mark formed portion and j is an integer representing any of 1 to k to n.)

A peak value representing a roll mark is suppressed by the above smoothing processing, and an autocorrelation value corresponding to the background power is calculated. Smoothed output E29 (=$\overline{Cmk}$) from smoother 29 is supplied to roll mark detection level generator 30.

Roll mark detection level generator 30 multiplies smoothed output E29 ($\overline{Cmk}$) of each row with a predetermined number ($\alpha$ or $1+\alpha$) and supplies the multiplied output as roll mark detection level L* (FIG. 2) corresponding to a background power level to comparator 21.

Comparator 21 sequentially compares autocorrelation value data of each row, e.g., C1e, C2(e+1) to C1n with level L* of each row from generator 30, and outputs a maximum value in the autocorrelation value data of each row found as a result of comparison. This comparison calculation is performed to each autocorrelation value data for automatic judgment of roll mark inspection.

Comparator 21 is connected to channel selector 25 having contacts 25-1, 25-2, ..., 25-m for the respective rows. Selector 25 is connected to interface 26 and then to detect (roll mark) display device 27. The signal output from interface 26 is also supplied, as an automatic roll make judgment signal, to external host CPU (computer) 33.

Comparator 21 performs roll mark detection processing in accordance with either the following equation (11A) or (11B):

$$X = (Cmk - \overline{Cmk}) - \alpha\overline{Cmk} \quad \ldots (11A)$$

$$X = CMK - (1+\alpha)\overline{Cmk} \quad \ldots (11B)$$

where $\alpha$ is generally 2 or 3. $\overline{Cmk}$ in equation (11A) or $(1+\alpha)$Cmk in equation (11B) represents roll mark detection level L*.

In comparator 21, if X in equation (11A) or (11B) is 0 or negative, data Cmk is determined to include no roll mark. If X is positive, an automatic judgment is made such that data Cmk includes roll mark(s). This automatic judgment can be made in host CPU 33.

Figure 11B:
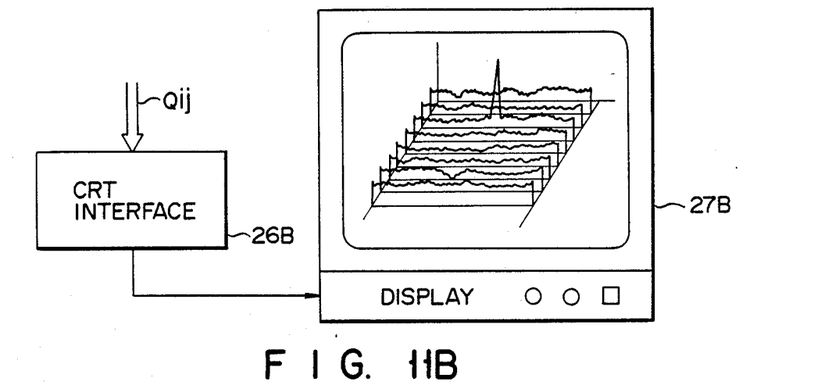
FIG. 11B shows a configuration for performing the 3D graphic display using the embodiment of FIG. 11A.

FIG. 11B shows a 2D/3D display device adapted to the configuration of FIG. 11A. Data Qij from profile memory 28 in FIG. 11A is supplied to CRT display 27B, via CRT interface 26B. (An engineering workstation for CAD/CAM can be applied to such a 2D/3D display device.)

The length of the strip used for the automatic roll mark judgment is selected to be, for example, 1000 m. Each time this judgment is done, the pattern of FIG. 9 (2D) or FIG. 10 (3D) is displayed on display device 27B of FIG. 11B.

Figure 10:
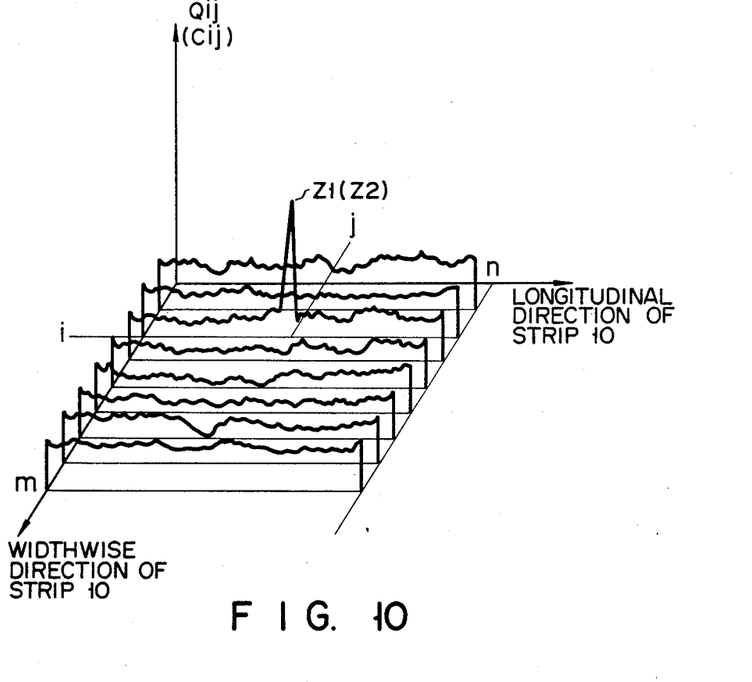
FIG. 10 is a 3D graph three-dimensionally showing autocorrelation values Cij of 1st to mth columns in the width direction of strip 10.

FIG. 10 shows such a three-dimensional display. In order to perform the three-dimensional display in this manner, data Qij in memory 28 instead of data Cij can be used as three-dimensional display data.

An operation of the apparatus having the above arrangement will be described below. When strip 10 in FIG. 11A runs in the arrow direction, head 11 optically scans strip 10 widthwise and outputs roll mark signal E11 to binary circuit 12A and noise level detector 12B. Detector 12B detects and supplies noise level E12B to circuit 12A. Circuit 12A produces a variable binary set level (binarizing or digitizing threshold level) in accordance with level E12B so as to binarize or digitize the magnitude of signal E11, and supplies the binary signal as roll mark data E12 which is then stored in register 13. The roll mark data is stored as one column of data S10 to Sm0 (i.e., roll mark data of pixels $\Delta\omega \times m$) widthwise of strip 10 in synchronism with sync signal CK in register 13. Each time strip 10 runs by unit length $\Delta\tau$, the next roll mark data of one column widthwise of strip 10 is sequentially stored in register 13 by signal CK.

Each time the roll mark data of one column widthwise is supplied to register 13 as described above, preceding roll mark data stored in register 13 is parallel output to image memory 15. Each time memory 15 receives the roll mark data of one column, memory 15 parallel shifts stored roll mark data of one column. Each time strip 10 runs by roll circumferential length $\Delta\tau$, the roll mark data of one column is output to compensator 15X and then to autocorrelation calculator 16.

Multiplier 17 in calculator 16 multiplies the roll mark data of one column (e.g., S1n, S2n, ..., Smn) from memory 15 by the roll mark data of one column (S10, S20, ..., Sm0) from register 13 in units of pixels, and supplies multiplication results to adder 18. Adder 18 adds calculation results (e.g., C1n, C2n, ..., Cmn) from calculated value register 19 to the multiplication results from multiplier 17 in units of pixels, and supplies addition results to register 19. In this manner, register 19 stores the calculated values of the right-hand side of equation (4).

When counter 28A detects, by counting signals CK output from generator 14, that strip 10 runs by 1000 m, for example, calculated results C1e to Cmn stored in register 19 are supplied to autocorrelation profile memory 29. At this time, values C1e to C1n, for example, correspond to $\Sigma\phi ak$ shown in FIG. 2. These values are increased as inspection length $\tau$ is reduced, and the values are reduced as length $\tau$ is increased.

When strip 10 runs 1,000 m, smoother 29 performs the smoothing processing represented by equation (10) to addition value $\Sigma\phi ak$ of the calculation results of each row and supplies smoothed output E29 to roll mark detection level generator 30. Generator 30 multiplies output E29 of each row with a predetermined value and supplies the multiplied output as roll mark detection level L* to comparator 21.

Comparator 21 compares value $\Sigma\phi ak$ of the autocorrelation values of each row with level L* of each row as shown in FIG. 2. In this case, if selector 25 is connected to 25-1, a comparison result of value $\Sigma\phi ak$ with level L* is supplied to external host CPU 33 or to external display 27B for monitoring detects or roll marks of strip 10.

If selector 25 is automatically connected to 25-2 and the scanning by head 11 is performed, a comparison result of value $\Sigma\phi bk$ (not shown) with level L* is supplied to external device 27 or to external host CPU 33, via interface 26.

As described above, in this embodiment, the autocorrelation values obtained in the predetermined inspection length are smoothed by smoother 29. Smoothed output E29 is multiplied with a predetermined number by roll mark detection level generator 30 and supplied, as a roll mark detection level corresponding to a background power level, to comparator 21. With this arrangement, regardless of the value of inspection length $\tau$, any roll mark can be reliably inspected without being adversely affected by the background power level. In addition, since noise level detector 12B generates the variable binary set level of binary circuit 12A, a variation at low frequencies in background noise level can be suppressed to be a predetermined level. For this reason, an image with a fixed S/N ratio can be displayed on the screen of display device 27 (or 27B). Therefore, not only an automatic judgment of periodic detects (roll marks) can be made with a fixed S/N ratio, but also roll marks can be inspected on the CRT display screen with improved high quality to sufficiently achieve a roll mark inspection function.

As has been described in detail above, the embodiment of the present invention can provide a roll mark inspection apparatus capable of inspecting all periodic roll marks without being adversely affected by the background power.

Figure 12A:
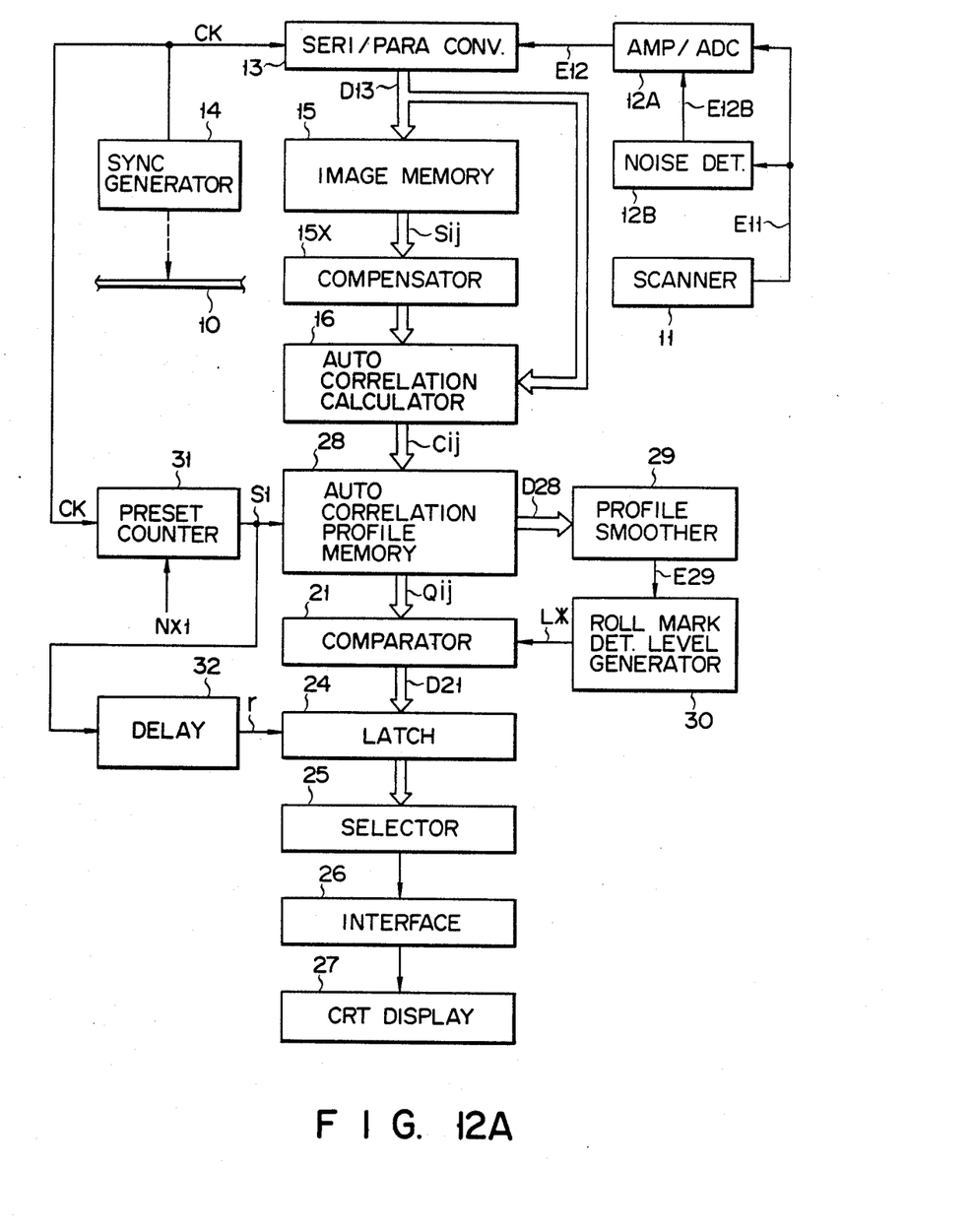
FIG. 12A is a block diagram showing an arrangement of a roll mark inspection apparatus according to a third embodiment of the present invention.

FIG. 12A shows still another embodiment of the present invention adopting the embodiments in FIGS. 1 and 11A in combination. In the apparatus shown in FIG. 12A, roll mark signal E12 obtained by binarizing output E11 from inspection head (scanner) 11 in accordance with its background power level is fetched by register (serial/parallel converter) 13 by clock CK synchronized with running of strip 10.

Signal E12 fetched in register 13 is converted into parallel roll mark data D13 and data D13 is sequentially fetched by image memory 15 in synchronism with clock CK.

Data Sij fetched in memory 15 is supplied to compensator 15X and then to autocorrelation calculator 16. Calculator 16 receives data D13 from register 13 and performs autocorrelation calculation. Calculation result Cij is supplied to autocorrelation profile memory 28 at each time when output S1, representing that strip 10 runs by a predetermined distance (e.g., $\pi d2$), is generated from counter 31. Preset number Nx1 of counter 31 represents diameter d2 of roll R2.

Data D28 (Q1e to Qmn) of autocorrelation calculation result Cij is supplied from profile memory 28 to profile smoother 29, and calculated therein in accordance with equation (10) to be converted into smoothed output E29 ($\overline{Cmk}$).

Output E29 is supplied to roll mark detection level generator 30. Generator 30 calculates roll mark detection level L* corresponding to $\overline{Cmk}$ of the right-hand side of equation (11A) or (11B) from output E29 and predetermined magnification $\alpha$, and supplies it to comparator 21.

Comparator 21 compares total sum $\Sigma\phi ak$ of autocorrelation values as shown in FIG. 2 with level L*, and comparison result D21 is loaded in latch 24. This loading is performed by signal r. Signal r is obtained by delaying the phase of output S1 from counter 31 by delay circuit 32.

Of the data loaded on latch 24, data representing a portion of strip 10 to be inspected (e.g., an mth column portion) is selected by selector 25. The selected data is supplied to CRT display device 27 through interface 26 so that a roll mark pattern of the portion to be inspected of strip 10, as is shown in FIG. 3, is displayed on device 27.

Figure 12B:
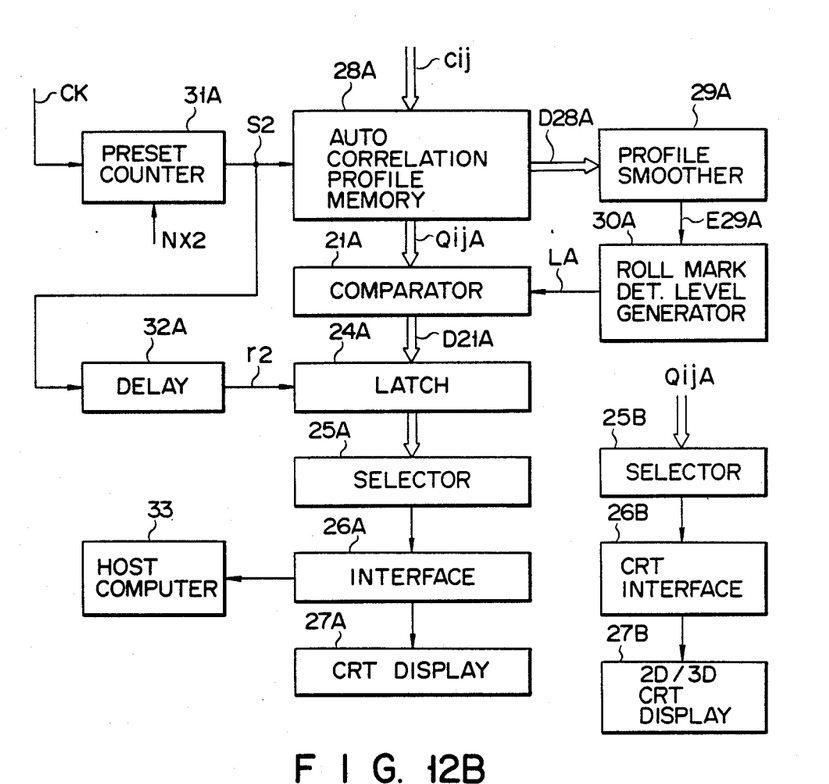
FIG. 12B shows an additional configuration adapted to the embodiment of FIG. 12A.

In the arrangement of FIG. 12B, number Nx2 representing, e.g., 1000 m of strip 10, is preset to counter 31A. Counter 31A down-counts clock CK from sync generator 14 (FIG. 12A) and, when the count reaches "0", supplies signal S2 to another autocorrelation profile memory 28A.

Autocorrelation calculation result Cij delivered from autocorrelation calculator 16 (FIG. 12A) is fetched by profile memory 28A in accordance with the timing of generation of signal S2. Data D28A of autocorrelation calculation result Cij is supplied from profile memory 28A to profile smoother 29A.

Smoother 29A effects calculation on data D28A according to equation (10), and result E29A of the calculation is input to roll mark detection level generator 30A. Generator calculates roll mark detection level LA corresponding to $\overline{Cmk}$ in equation (11A) or (11B), and supplies it to comparator 21A.

Comparator 21A compares each content of data QijA delivered from profile memory 28A with detection level LA, and result D21A of the comparison is loaded into latch 24A. This loading is performed at the timing of generation of signal r2. Signal r2 is obtained by delaying the phase of signal S2 by delay circuit 32A.

Similar to the embodiment of FIG. 1, a prescribed part of the contents in latch 24A is selected by selector 25A, and the selected data is sent to CRT display 27A as well as to host computer 33, via interface 26A. Display 27A and computer 33 are used for automatic judgment of the roll mark.

A prescribed part of the contents of data QijA from profile memory 28A is selected by selector 25B, and the selected data is supplied, via CRT interface 26B, to 2D/3D CRT display 27B as is shown in FIG. 11B. Display 27B displays the pattern as shown in FIG. 9 (2D) or in FIG. 10 (3D).

An operator of this inspection apparatus can immediately check whether a roll mark is formed on strip 10 by observing patterns as shown in FIG. 3, 9, or 10. In addition, by checking an interval in a time axis direction (left-to-right direction on the CRT display screen) of the roll marks (Z1 and Z2) of the displayed patterns using a scale (27S) or the like, the operator can immediately know which rolls R1 and R2 (FIG. 1 or 11A) cause the roll mark.

The present invention is not limited to the above embodiments but can be modified without departing from the spirit and scope of the present invention. For example, in the above embodiments, roll mark detection level L* is binarized by comparator 21. However, a plurality of levels L may be set to form a multilevel value. In addition, profile smoother 29 may receive calculation results C1e to Cmn obtained each time strip 10 runs by roll circumferential length $\pi d2$ and performs the smoothing processing so that the autocorrelation values are compared with roll mark detection level L* each time strip 10 runs by length $\pi d2$.

What is claimed is:

1. A roll mark inspection apparatus, which is applied to a system for rolling and moving a strip material using reduction rolls, comprising:
    surface state inspecting means for outputting an image signal representing a surface state of said strip material rolled and moved by said reduction rolls;
    image information processing means connected to said surface state inspecting means for receiving the image signal output from said surface state inspecting means in synchronism with running of said strip material, performing predetermined processing to the received information, and outputting processed information;
    comparing means connected to said image information processing means for comparing a predetermined comparison value, used to extract information corresponding to roll marks formed on the surface of said strip material by a speck of said reduction rolls, with the processed information output from said image information processing means, and outputting information discriminated from the processed information by the predetermined comparison value, and
    display means connected to said comparing means for displaying an image corresponding to the discriminated information output from said comparing means each time said strip material runs by a predetermined distance corresponding to a circumferential length of said reduction rolls.

2. The apparatus according to claim 1, wherein said display means includes:
    clock signal generating means for generating a clock signal in synchronism with running of said strip material;
    latch means for storing the discriminated information each time a predetermined number of the clock signals are generated; and
    display device for displaying an image corresponding to the roll mark of said belt-like material on a basis of the information latched in said latch means.

3. The apparatus according to claim 1, wherein said comparing means includes:
    smoothing signal generating means for detecting an average value per predetermined running distance of said strip material of contents of the processed information output from said image information processing means, and generating a smoothed signal corresponding to the detected average value;
    detection level generating means for generating from the smoothed signal a roll mark detection level which changes in correspondence with signal components not caused by the roll mark of the image signal representing the surface state of said strip material; and
    supplying means for comparing the contents of the processed information with the roll mark detection level, and supplying a comparison result as the discriminated information to said display means.

4. The apparatus according to claim 1, wherein said surface state inspecting means includes:
    image sensor means for scanning the surface of said strip material widthwise, and outputting a surface state signal representing the surface state;
    binary set level generating means for generating a binary set level which changes in correspondence with a noise signal component included in the surface state signal from said image sensor means; and
    means for producing a binary form of the surface state signal and outputting the image signal on a basis of the binary set level.

5. The apparatus according to claim 1, wherein said display means includes:
    a direct-view display device for displaying an image corresponding to the roll mark of said strip material on the basis of a discriminated information output from said comparing means; and
    a scale, mounted on a display screen of said direct-view display device, for reading one of points and a period of the generated roll mark.

6. The apparatus according to claim 1, wherein said image information processing means includes:
    an autocorrelation function converting means for converting information corresponding to the image signal represented as a function f(t) into an autocorrelation function $\phi(\tau)$ $\tau$ corresponding to a circumferential length of said reduction roll, the autocorrelation function $\phi(\tau)$ being substantially represented by either of the following equations assuming that an interval for obtaining the autocorrelation is T:

$$\phi(\tau) = \lim_{T\to\infty}(1/2T) \int_{-t}^{+t} f(t) \cdot f(t+\tau) \cdot dt$$

$$\phi(\tau) = \lim_{T\to\infty}(1/T) \int_{0}^{t} f(t) \cdot f(t+\tau) \cdot dt,$$

and the processed information being output from said autocorrelation function converting means.

7. The apparatus according to claim 6, wherein said image signal processing means further includes:
converting means for converting the image signal in a form of serial data into parallel image data; and
memory means for sequentially storing the parallel image data in synchronism with running of said strip material, the image signal and the parallel image data read out from said memory means being supplied as input data of autocorrelation function calculation to said autocorrelation function converting means.

8. The apparatus according to claim 6, wherein said image information processing means includes:
image memory means for storing image information included in the image signal and representing a predetermined range on the surface of said strip material, the image information read out from said image memory means being supplied to said autocorrelation function converting means.

9. The apparatus according to claim 6, wherein said image information processing means includes:
image memory means for storing two-dimensional image information included in the image signal and representing a predetermined range on the surface of the strip material; and
compensating means for performing compensating processing for substantially removing a periodic change included in the image signal from the two-dimensional image information read out from said image memory means, and supplying the compensated information to said autocorrelation function converting means.

10. The apparatus according to claim 1, wherein said display means includes:
means for one of two-dimensionally and three-dimensionally displaying the information corresponding to the image signal.

11. A roll mark inspection apparatus which is applied to a system for rolling and moving a strip material using reduction rolls, comprising:
first means for scanning widthwise said strip material rolled and moved by said reduction rolls, and outputting a first signal representing a surface state of said strip material;
second means for generating a second signal synchronized with running of said strip material moved by said reduction rolls;
third means for sequentially receiving the first signal in synchronism with the second signal, and outputting a third signal obtained by performing predetermined autocorrelation calculation processing to contents of the received signal;
fourth means for comparing a predetermined comparison level for discriminating information corresponding to a roll mark on the surface of said strip material with the third signal, and outputting a fourth signal discriminated from the third signal by the predetermined comparison value; and
fifth means for updating and displaying image information corresponding to the fourth signal each time said strip material runs by a predetermined distance corresponding to a circumferential length of said reduction rolls.

12. The apparatus according to claim 11, wherein said fifth means includes:
clock signal generating means for generating a clock signal in synchronism with running of said strip material;
latch means for storing the fourth signal each time a predetermined number of clock signals are generated; and
display device for displaying an image corresponding to the roll mark of said strip material on a basis of the fourth signal latched in said latch means.

13. The apparatus according to claim 11, wherein said fourth means includes:
smoothing signal generating means for detecting an average value per predetermined running distance of said strip material of contents of the third signal output from said third means, and generating a smoothed signal corresponding to the detected average value;
detection level generating means for generating from the smoothed signal a roll mark detection level which changes in correspondence with signal components not caused by the roll mark of the first signal representing the surface state of said strip material; and
supplying means for comparing the contents of the third signal with the roll mark detection level, and supplying a comparison result as the fourth signal to said display means.

14. The apparatus according to claim 11, wherein said first means includes:
image sensor means for scanning the surface of said strip material widthwise, and outputting a surface state signal representing the surface state;
binary set level generating means for generating a binary set level which changes in correspondence with a noise signal component including in the surface state signal from said image sensor means; and
means for producing a binary form of the surface state signal and outputting the first signal on a basis of the binary set level.

15. The apparatus according to claim 11, wherein said fifth means includes:
a direct-view display device for displaying an image corresponding to the roll mark of said strip material on a basis of the fourth signal output from said fourth means; and
a scale, mounted on a display screen of said direct-view display device, for reading one of points and a period of the generated roll mark.

16. The apparatus according to claim 11, wherein said third means includes:
an autocorrelation function converting means for converting information corresponding to the first signal represented as a function f(t) into an autocorrelation function $\phi(\tau)$ corresponding to a circumferential length of said reduction roll, the autocorrelation function $\phi(\tau)$ being substantially represented by either of the following equations assuming that an interval for obtaining the autocorrelation is T:

$$\phi(\tau) = \lim_{T\to\infty}(1/2T) \int_{-t}^{+t} f(t) \cdot f(t + \tau) \cdot dt$$

$$\phi(\tau) = \lim_{T\to\infty}(1/T) \int_{0}^{t} f(t) \cdot f(t + \tau) \cdot dt,$$

and the third signal being output from said autocorrelation function converting means.

17. The apparatus according to claim 16, wherein said third means further includes:
converting means for converting the first signal in a form of serial data into parallel image data; and
memory means for sequentially storing the parallel image data in synchronism with running of said strip material, the image signal and the parallel image data read out from said memory means being supplied as input data of autocorrelation function calculation to said autocorrelation function converting means.

18. The apparatus according to claim 16, wherein said third means includes:
image memory means for storing image information included in the first signal and representing a predetermined range on the surface of said strip material, the image information read out from said image memory means being supplied to said autocorrelation function converting means.

19. The apparatus according to claim 16, wherein said third means includes:
image memory means for storing two-dimensional image information included in the first signal and representing a predetermined range on the surface of the strip material; and
compensating means for performing compensating processing for substantially removing a periodic change included in the first signal from the two-dimensional image information read out from said image memory means, and supplying the compensated information to said autocorrelation function converting means.

20. The apparatus according to claim 11, wherein said display means includes:
means for one of two-dimensionally and three-dimensionally displaying the information corresponding to the first signal.

21. A roll mark inspection apparatus which receives roll mark data from an inspection head for scanning widthwise a strip running material rolled and moved by rolls and stores the roll mark data in an image memory having a storage area corresponding to a circumferential length of said rolls, sequentially reads out the roll mark data stored in said memory in synchronism with a running rate of said strip running material to calculate an autocorrelation value, and compares the autocorrelation value with a set value by a comparator, thereby inspecting a periodic roll mark formed on said strip running material, comprising:
a sync signal generator for generating a sync signal synchronized with the running rate of said strip running material;
latch means connected to said sync signal generator for receiving the sync signal from said sync signal generator to detect that said strip running material runs by the roll circumferential length, and latching a comparison result output from said comparator; and
display means connected to said latch means for causing a CRT display device to display the comparison result output latched by said latch means as one raster.

22. A roll mark inspection apparatus which receives roll mark data from an inspection head for scanning in a width direction a strip running material rolled and moved by rolls and stores the roll mark data in an image memory having a storage area corresponding to a circumferential length of said rolls, calculates an autocorrelation value of the roll mark data obtained in a predetermined inspection length in a running direction of said strip running material, and converts the autocorrelation value into a binary value in accordance with a roll mark detection level by a comparator, thereby inspecting a periodic roll mark formed on said strip running material by a roll mark present on the surface of said rolls, comprising:
a smoother for smoothing the autocorrelation value obtained in the predetermined inspection length; and
a roll mark detection level generator connected to said smoother for multiplying a smoothed output from said smoother with a predetermined number, and supplying the multiplied output as a roll mark detection level corresponding to a background power level to said comparator.

* * * * *